United States Patent [19]
Wiedemann et al.

[11] Patent Number: 5,776,233
[45] Date of Patent: Jul. 7, 1998

[54] PROCESS FOR PREPARING A CERAMIC MATERIAL FOR USE IN DENTAL FILLINGS AND DENTAL CROWNS

[75] Inventors: Wolfgang Wiedemann, Höchberg; Hans Georg Klinger, Rossbrunn, both of Germany

[73] Assignee: BEGO Bremer Goldschlagerei Wilh. Herbst GmbH & Co., Bremen, Germany

[21] Appl. No.: 243,071

[22] Filed: May 13, 1994

Related U.S. Application Data

[63] Continuation of Ser. No. 873,947, Apr. 24, 1992, abandoned.

[51] Int. Cl.[6] .............................. A61F 1/24; C09K 3/00; C04B 35/00; A61K 5/01
[52] U.S. Cl. .................. 106/35; 501/1; 501/3; 501/12; 501/10; 423/305; 423/307; 423/315
[58] Field of Search .................. 501/1, 12, 3, 10; 106/35; 423/305, 315, 307

[56] References Cited

U.S. PATENT DOCUMENTS

| 4,097,935 | 7/1978 | Jarcho | 106/35 |
| 4,135,935 | 1/1979 | Pfeil et al. | 106/35 |
| 4,149,893 | 4/1979 | Aoki et al. | 106/35 |
| 4,376,168 | 3/1983 | Takani et al. | 501/1 |
| 5,091,344 | 2/1992 | Enomoto et al. | 501/1 |

FOREIGN PATENT DOCUMENTS

| 2534505 | 2/1976 | Germany. |
| 3831260 | 3/1989 | Germany. |
| 3912379 | 10/1989 | Germany. |

*Primary Examiner*—Melissa Bonner
*Attorney, Agent, or Firm*—Edwin D. Schindler

[57] ABSTRACT

A bioactive ceramic material for dental fillings and crowns on the basis of calcium phosphate compounds contains crystallites of sparingly water-soluble calcium phosphate compounds in an amorphous, vitreous or polycrystalline matrix of readily water-soluble calcium phosphate compounds, the Ca/P-atomic ratio of the calcium phosphate compounds being altogether <1.65.

20 Claims, 1 Drawing Sheet

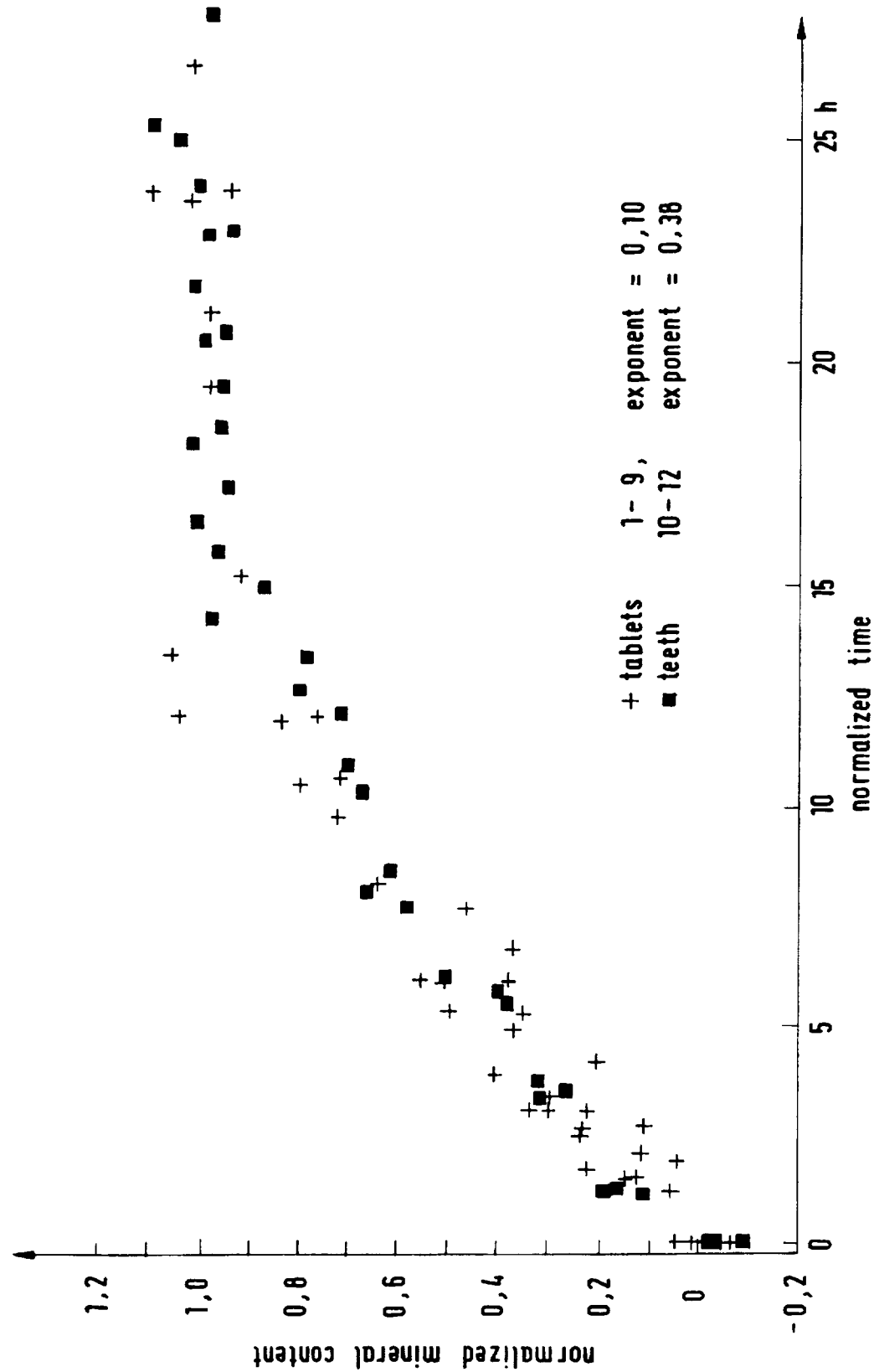

PROCESS FOR PREPARING A CERAMIC MATERIAL FOR USE IN DENTAL FILLINGS AND DENTAL CROWNS

This is a Continuation of application Ser. No. 07/873,947, filed Apr. 24, 1992, now abandoned.

BACKGROUND OF THE INVENTION

The invention relates to a bioactive ceramic material for indirect dental fillings, for example inlays, and dental crowns.

The natural dental enamel is made of prisms which extend from the dentine to the surface of the enamel. Each of these prisms is formed from a plurality of apatite crystallites which are connected to one another by a polycrystalline bonding layer, i.e. the so-called interprismatic substance.

To fill up carious defects in the dental enamel, moldable materials such as amalgams, inorganic cements and plastics which harden in the prepared cavity of the tooth are normally used. Another means for restoring carious defects are cast fillings made of metal, for example gold. Ceramic masses are increasingly employed as well. These masses are either modelled individually on a stump made from an impression or they are cast in the form of a so-called glass-ceramic or they are cut from the ceramic material with a computer-controlled tool.

SUMMARY OF THE INVENTION

These conventional materials have drawbacks, some of which being very substantial. Amalgam may cause allergies; the discussion about the hazards of mercury is still not concluded. There is, however, no doubt about the additional pollution of the environment with mercury. Gold is no doubt a valuable filling material, but very expensive. Plastics do not possess the required mechanical properties, especially for the lateral tooth portions. An extensive use of plastics is therefore not recommended. Ceramic masses as they are conventionally used in dentistry also differ from dental enamel with regard to their mechanical properties. They are, for example, more resistant to abrasion than dental enamel and may thus damage the antagonist.

In daily use, teeth are subjected to a constant change between high and low temperatures and between an acidic and an alkaline environment. All conventionally used restoration materials have in common that their physical properties such as heat conductability, thermal coefficient of expansion, modulus of elasticity, water absorption, shrinkage and expansion differ from the respective properties of the dental enamel in a more or less substantial manner. Especially the differences in thermal expansion lead to relatively early signs of material fatigue on the filling material itself and on the transition to the dental enamel.

It is known in the field of implantology to use hydroxyapatite ($Ca_5(PO_4)_3(OH)$) for the treatment of bone defects and for tooth implants; see for example DE-OS 35 31 144. But the profile of characteristics required from such implant materials is fundamentally different from that of the materials for dental fillings and crowns. In particular, the implant materials have to be insoluble which means that, as result of the lack of an active surface, the remineralisation which is needed for filling materials can not take place.

It is the object of the invention to provide a material for indirect dental fillings and dental crowns whose mechanical and physico-chemical properties are similar to those of the natural dental enamel.

BRIEF DESCRIPTION OF THE DRAWING

The drawing is a graph showing the increase in mineral content as a function of time for a ceramic material prepared in accordance with the process of the invention.

The subject matter of the invention is a bioactive ceramic material for dental fillings and crowns on the basis of calcium phosphate compounds, which is characterized in that it contains crystallites of sparingly water-soluble calcium phosphate compounds in an amorphous, vitreous or polycrystalline matrix of readily water-soluble calcium phosphate compounds, the Ca/P atomic ratio of the calcium phosphate compounds being altogether <1.65.

Because of its dental enamel-like structure, the ceramic material according to the invention has the same demineralisation and remineralisation behavior as natural dental enamel, which means that there is an acid-conditioned softening of the top layer with a large active surface in the pores, and subsequently a rehardening caused by remineralisation as a result of the ion exchange with the saliva which contains calcium phosphate.

The material, which was originally calcium deficient—with respect to hydroxyapatite (Ca/P atomic ratio: 1.67)—is first of all partially dissolved when it is introduced into the prepared cavity of the tooth, in which process the readily soluble matrix phase formed from calcium phosphates such as monetite or brushite starts to dissolve and top surface pores are formed. This corresponds to the demineralisation of the dental enamel caused by acids which usually takes place in the buccal cavity.

But because of a contact with solutions, such as saliva or applied remineralisation media, which are supersaturated with calcium phosphates, a remineralisation takes place which results from a growth or new formation of hydroxyapatite crystallites. Consequently, the pores close up again and, finally, a filling material which is comparable to natural hydroxyapatite is present in the filled cavity. The biological activity of the ceramic material according to the invention is based on this process.

The use of calcium deficient materials and the subsequent natural or artificial remineralisation and forming of hydroxyapatite has the particular advantage that the dental filling material as well as the parting line between dental filling material and dental enamel or dentine consists of a material which has the same mechanical and physico-chemical properties as the dental enamel itself.

When the ceramic material according to the invention is used for dental fillings and crowns, the filling or crown enters into a firm and homogenous crystalline combination with the inorganic phase of the dental enamel, so that the forming of crackle, as it occurs for example with gold inlays, is avoided. Moreover, the electrochemical potential of filling and dental enamel is the same. Besides, allergic reactions are ruled out, because the material is composed of calcium and phosphate ions which are ubiquitious in the body.

The ceramic material according to the invention contains a sparingly soluble crystallite phase composed of calcium phosphates such as hydroxyapatite ($Ca_5(PO_4)_3(OH)$), fluoroapatite ($Ca_5(PO_4)_3F$) or mixtures thereof, in a readily soluble matrix phase composed of calcium phosphate compounds such as brushite ($CaHPO_4 \times 2H_2O$), monetite ($CaHPO_4$), carbonate apatite (see WO 86/01726), tricalcium phosphate, octacalcium phosphate ($Ca_8H_2(PO_4)_6 \times 5H_2O$) or mixtures thereof.

For the purpose of this invention, "sparingly soluble" thus means a solubility in water which is comparable to hydroxyapatite, whereas "readily soluble" means a solubility which is relatively higher than the solubility of hydroxyapatite.

Compared to pure hydroxyapatite, the ceramic material according to the invention has a calcium deficit, which means that the Ca/P atomic ratio is <, but not including 1.65 and preferably ranges from 1.2 to 1.65, especially from 1.5 to but not including 1.65, in each case calculated on the basis of the calcium phosphate compounds which are contained therein.

The demineralisation and remineralisation behavior of the ceramic material is essentially influenced by the size and orientation of the crystallite phase and by the composition of the matrix phase. A specific surface which is as large as possible during demineralization and an elasticity and brittleness (breaking behavior) which is comparable to the dental enamel can be attained by varying the crystallite size, the crystallite proportion and the composition of the matrix phase.

Preferably, 70 to 98, especially 80 to 95 percent by weight of the calcium phosphate compounds of the ceramic material consist of crystallites of the sparingly soluble proportion. The crystallites usually have a size of 0.1 to 100 µm, preferably 0.5 to 50 µm.

If required, the ceramic material may be provided with anisotropic properties, for example by means of an addition of crystal habit modifiers, crystal growth inhibitors and by means of processing techniques, in order to selectively allow for the local variations of the cariogenous environment around the tooth.

If required, the ceramic material according to the invention may, apart from the calcium phosphate compounds, also contain conventional additives, for example fluorine compounds such as NaF, $CaF_2$ or $Na_2PO_3F$; organic binding agents such as polyacrylates, polyester, polysaccharides and polypeptides; inorganic binding agents such as silicates, aluminium oxide, cements or silicons; pigments and dyes. Reinforcing filler materials and fibres, for example silicon carbide or phosphate fibres, may be added to increase the strength of the material for dental crowns. Preferred are reinforcing filler materials and fibres with a higher thermal coefficient of expansion than hydroxyapatite, because they create a compressive strain which increases the strength.

The ceramic material according to the invention can for example be prepared by grinding one or several sparingly water-soluble calcium phosphate compounds and one or more readily water-soluble calcium phosphate compounds with a weight ratio which corresponds to a Ca/P atomic ratio of <1.65 to a particle size of <30 µm, usually 0.5 to 20 µm and preferably 1 to 10 µm.

Alternatively, calcium phosphate compounds may be precipitated from an aqueous solution of calcium compounds and phosphate compounds, for example by means of adding a base such as NaOH, KOH or $NH_4OH$. The quantity ratios of the parent compounds are in this case selected such that the desired calcium deficient product is formed. Subsequently, this product is separated, for example by filtration, and is dried and, if required, comminuted.

In a preferred embodiment of the latter process, the precipitation of the calcium phosphate compounds is conducted according to the sol-gel method in aqueous or aqueous/organic, for example aqueous/alcoholic media by means of a gradual addition of the basic precipitating agent.

The product obtained by grinding or precipitating is then compressed under pressures of for example 1000 to 6000 kg/cm² into green compacts and is sintered at temperatures of 800° to 1400° C., preferably 1100° to 1200° C. Sintering may for example be conducted for 15 minutes to 24 hours under normal or increased pressure. During compressing and sintering, the calcium phosphate phases are partially melted open and at the same time form crystallites.

The ceramic material which is formed may then be made (for example cut) into dental fillings (inlays) or dental crowns in the usual way.

The filling may be incorporated into the prepared cavity of the tooth in different ways. In a preferred embodiment, the dental filling is made with a slight oversize (of up to 100 µm), subsequently softened on the surface by means of a treatment with acid (for example acetic acid) and is then pressed into the cavity.

Alternatively, the dental filling may be cemented in the cavity with a mineralisable cement, for example with the cement described in U.S. Pat. No. 4,518,430, or with another conventional cement, for example a zinc-oxide phosphate cement or preferably a glas ionomer cement.

Within a few hours (approximately 10 to 15 hours) after the incorporation of the calcium deficient ceramic material into the dental cavity, a remineralisation takes place because of an ion transfer with the saliva or an applied remineralisation liquid. In this process, a material is formed, especially in the parting line, which has mechanical and physicochemical properties like those of the dental enamel.

The following example illustrates the invention.

EXAMPLE

Analogous to the production method given by Anderson and Elliott (Caries. Res. 19, 403–406, 1985), 0.246 mol/l $(NH_4)_2HPO_4$ are set to pH 10 with ammonia. 0.8 liters of this solution are added dropwise at 70° C. to 4 liters of a $Ca(NO_3)_2$ solution which contains 0.082 mol/l and which is also set to pH 10.

At the end of the precipitation, a pH of 7 has established. The solution with the precipitate is stirred at 70° C. for 24 h. After the solution has cooled, it is decanted and the precipitate is washed six times in 5 l deionized water at 70° C. (1 h), filtered off and dried at 200° C. The mass is comminuted in a mortar. Green compacts are compressed from the powder under a pressure of 1500 kg/cm² and are then sintered for 3 h at 1100° C.

The density of the obtained material amounts to 95% of the density of crystalline hydroxyapatite. An examination of the structure under the light-optical microscope shows a phase which is readily soluble in acid and in which rod-shaped crystallites of approximately 0.5 to 1 µm length are stored in a tightly packed manner.

Nine sintered compacts which have been prepared in this way were surface-ground and polished. Thereafter, the relative mineral content was determined via the microhardness (Featherstone et al. Caries. Res. 17, 385–391, 1983). Additionally, enamel bevels were cut into three teeth. Both groups of samples were each incubated in 8 ml 1 n acetic acid which contained 2.5 mmol/l $(Ca_5(PO_4)_3(OH))$ for 1 h (dental enamel) and 2 h (sintered compact), respectively. During this period, the mineral content in the surface layer decreased to an average of 52% (teeth) and 44% (sintered compact), respectively. In the artificial saliva (composed according to the specifications in Documenta Geigy, Scientific Tables, Ed.: Geigy AG, Basel, 1975), remineralisation took place with the addition of 50 ppm sodium fluoride.

The increase of the relative mineral content is specified in the drawing. The almost linear increase of the mineral content with respect to the sintered compacts is concluded after an average of 13 h, the increase with respect to the enamel samples is parabolic. They reach their initial hardness after approximately 20 h.

We claim:

1. A process for preparing a ceramic material for dental purposes, comprising the steps of:

making calcium phosphate compounds from an aqueous solution of at least one calcium compound by adding at least one phosphate compound, and precipitating calcium phosphate compounds from the aqueous solution under such conditions that the Ca/P-atomic ratio is <1.65 wherein the solution is initially set to a pH value of 10 which reduces to a value of 7 during precipitation;

drying the precipitate and then comminuting it to produce a product and then compressing the product into green compacts and sintering them at temperatures of 800° to 1400° C. so that crystallites of sparingly water-soluble calcium phosphate compounds are created in an amorphous or polycrystalline matrix of readily water-soluble calcium phosphate compounds.

2. The process according to claim 1, wherein the precipitating step takes place in an aqueous/organic medium.

3. The process according to claim 1, wherein the precipitating step comprises gradually adding a basic precipitating agent.

4. The process according to claim 2, wherein the aqueous/organic medium is an aqueous/alcoholic medium.

5. The process according to claim 1, wherein the calcium phosphate compounds have a Ca/P atomic ratio in the range of from 1.2 to 1.65, not including 1.65.

6. The process according to claim 5, wherein the range is from 1.5 to 1.65, not including 1.65.

7. A process for preparing a ceramic material for dental purposes comprising the steps of:

making calcium phosphate compounds from an aqueous solution of at least one calcium compound by adding at least one phosphate compound, and precipitating calcium phosphate compounds from the aqueous solution under such conditions that the Ca/P-atomic ratio is <1.65;

drying the precipitate and then comminuting it to produce a product; and then compressing the product into green compacts and sintering them at temperatures of 800° to 1400° C.;

wherein the precipitating step takes place in an aqueous/ organic medium, wherein the precipitating step comprises gradually adding a basic precipitating agent, and wherein solutions of the calcium compound and the phosphate compound are each initially set to a pH value of 10, so that, after the precipitation of the calcium phosphate compounds, the pH value of the solution containing the precipitated calcium phosphate compounds is 7, and so that crystallites of sparingly water-soluble calcium phosphate compounds are created in an amorphous or polycrystalline matrix of readily water-soluble calcium phosphate compounds.

8. The process according to claim 7, wherein the aqueous/ organic medium is an aqueous/alcholic medium.

9. The process according to claim 8, wherein the calcium phosphate compounds have a Ca/P atomic ratio in the range of from 1.2 to 1.65, not including 1.65.

10. The process according to claim 9, wherein the range is from 1.5 to 1.65, not including 1.65.

11. A process for preparing a ceramic material for dental purposes, comprising the steps of:

making calcium phosphate compounds from an aqueous solution of at least one calcium compound by adding at least one phosphate compound, and precipitating calcium phosphate compounds from the aqueous solution under such conditions that the Ca/P-atomic ratio is <1.65 wherein the solution is initially set to a pH value of 10 which reduces to a value of 7 during precipitation;

drying the precipitate and then comminuting it to produce a product; and then compressing the product into green compacts and sintering them at temperatures of 800° to 1400° C. so that crystallites of sparingly water-soluble calcium phosphate compounds are created in a vitreous matrix of readily water-soluble calcium phosphate compounds.

12. The process according to claim 10, wherein the precipitating step takes place in an aqueous/organic medium.

13. The process according to claim 10, wherein the precipitating step comprises gradually adding a basic precipitating agent.

14. The process according to claim 11, wherein the aqueous/organic medium is an aqueous/alcoholic medium.

15. The process according to claim 10, wherein the calcium phosphate compounds have a Ca/P atomic ratio in the range of 1.2 to 1.65, not including 1.65.

16. The process according to claim 15, wherein the range is from 1.5 to 1.65, not including 1.65.

17. The process according to claim 11, wherein the precipitating step comprises gradually adding a basic precipitating agent.

18. The process according to claim 17, wherein the aqueous/organic medium is an aqueous/alcoholic medium.

19. The process according to claim 18, wherein the calcium phosphate compounds have a Ca/P atomic ratio in the range of from 1.2 to 1.65, not including 1.65.

20. The process according to claim 19, wherein the calcium phosphate compounds have a Ca/P atomic ratio in the range of from 1.5 to 1.65, not including 1.65.

* * * * *